US006500149B2

(12) United States Patent
Gandhi et al.

(10) Patent No.: US 6,500,149 B2
(45) Date of Patent: *Dec. 31, 2002

(54) APPARATUS FOR DEPLOYMENT OF MICRO-COIL USING A CATHETER

(76) Inventors: Deepak Gandhi, 911 Bowen Ave., San Jose, CA (US) 95123; Kamal Ramzipoor, 4543 Fellows St., Union City, CA (US) 94587; David A. Ferrera, 2001 Lynngrove Dr., Manhattan Beach, CA (US) 90266

( * ) Notice: Subject to any disclaimer, the term of this patent is extended or adjusted under 35 U.S.C. 154(b) by 0 days.

This patent is subject to a terminal disclaimer.

(21) Appl. No.: 09/790,983

(22) Filed: Feb. 21, 2001

(65) Prior Publication Data

US 2001/0029352 A1 Oct. 11, 2001

Related U.S. Application Data

(63) Continuation-in-part of application No. 09/501,466, filed on Feb. 9, 2000, which is a continuation-in-part of application No. 09/218,117, filed on Dec. 21, 1998, now Pat. No. 6,296,622, which is a continuation-in-part of application No. 09/143,904, filed on Aug. 31, 1998, now Pat. No. 6,224,610.

(51) Int. Cl.[7] ............................. A61F 7/12; A61F 11/00
(52) U.S. Cl. ...................................... 604/113; 606/108
(58) Field of Search ........................... 604/93.01, 95.05, 604/113, 164.03, 531; 606/108, 151, 191, 193, 194; 623/1.11, 1.23

(56) References Cited

U.S. PATENT DOCUMENTS

| 1,341,052 A | 5/1920 | Gale |
| 2,078,182 A | 4/1937 | MacFarland |
| 2,549,335 A | 4/1951 | Rahthus |

(List continued on next page.)

FOREIGN PATENT DOCUMENTS

| DE | 41 02 550 A1 | 8/1991 |
| EP | 0 183 372 A1 | 4/1986 |
| EP | 0 278 937 | 8/1988 |
| EP | 0 382 014 A1 | 8/1990 |
| EP | 0 518 704 A1 | 12/1992 |
| EP | 0 627 201 A1 | 12/1994 |
| FR | 592.182 | 7/1925 |
| GB | 2 066 839 A | 7/1981 |
| WO | WO 92/14408 | 9/1992 |
| WO | WO 94/16629 | 8/1994 |
| WO | WO 95/18585 | 7/1995 |
| WO | WO 95/21592 | 8/1995 |
| WO | WO 97/48351 | 12/1997 |

OTHER PUBLICATIONS

Christos A. Athanasoulis, M.D., The New England Journal of Medicine, May 15, 1980, "Therapeutic Applications of Angiography" pp. 1117–1125 (1 of 2).
Christos A. Athanasoulis, M.D., The New England Journal of Medicine, May 22, 1980, "Therapeutic Applications of Angiography" pp. 1174–1179 (2 of 2).
Alex Berenstein, M.D. and Irvin I. Kricheff, M.D., "Catheter and Material Selection for Transarterial Embolization: Technical Considerations" Radiology, Sep. 1979; pp. 631–639.
O.A. Battista, et al. Journal of Applied Polymer Science 1967 "Colloidal Macromolecular Phenomena. Part II. Novel Microcrystals of Polymers" pp. 481–498.

(List continued on next page.)

*Primary Examiner*—Michael J. Hayes

(57) ABSTRACT

The apparatus for deployment of a therapeutic device such as a micro-coil provides for a pusher member and a connector fiber for securing the therapeutic device to the pusher member. The connector fiber passes adjacent to a distal heating end of an elongated, flexible heat pipe member within the distal portion of the pusher member, for heating and breaking the connector fiber to release the therapeutic device when a desired placement of the therapeutic device within the vasculature is achieved.

17 Claims, 3 Drawing Sheets

U.S. PATENT DOCUMENTS

| | | |
|---|---|---|
| 3,334,629 A | 8/1967 | Cohn |
| 3,485,234 A | 12/1969 | Stevens |
| 3,649,224 A | 3/1972 | Anderson et al. |
| 3,868,956 A | 3/1975 | Alfidi et al. |
| 4,327,734 A | 5/1982 | White, Jr. |
| 4,341,218 A | 7/1982 | Ü |
| 4,346,712 A | 8/1982 | Handa et al. |
| 4,402,319 A | 9/1983 | Handa et al. |
| 4,441,495 A | 4/1984 | Hicswa |
| 4,494,531 A | 1/1985 | Gianturco |
| 4,503,569 A | 3/1985 | Dotter |
| 4,512,338 A | 4/1985 | Balko et al. |
| 4,545,367 A | 10/1985 | Tucci |
| 4,553,545 A | 11/1985 | Maass et al. |
| 4,611,594 A | 9/1986 | Grayhack et al. |
| 4,629,458 A | 12/1986 | Pinchuk |
| 4,638,803 A | 1/1987 | Rand |
| RE32,348 E | 2/1987 | Pevsner |
| 4,655,771 A | 4/1987 | Wallsten |
| 4,670,286 A | 6/1987 | Nyilas et al. |
| 4,718,907 A | 1/1988 | Karwoski et al. |
| 4,732,152 A | 3/1988 | Wallstén et al. |
| 4,748,986 A | 6/1988 | Morrison et al. |
| 4,768,507 A | 9/1988 | Fischell et al. |
| 4,795,458 A | 1/1989 | Regan |
| 4,798,606 A | 1/1989 | Pinchuk |
| 4,800,882 A | 1/1989 | Gianturco |
| 4,813,925 A | 3/1989 | Anderson, Jr. et al. |
| 4,820,298 A | 4/1989 | Leveen et al. |
| 4,830,003 A | 5/1989 | Wolff et al. |
| 4,850,960 A | 7/1989 | Grayzel |
| 4,856,516 A | 8/1989 | Hillstead |
| 4,873,978 A | 10/1989 | Ginsburg |
| 4,950,258 A | 8/1990 | Kawai et al. |
| 4,954,126 A | 9/1990 | Wallsten |
| 4,957,479 A | 9/1990 | Roemer |
| 4,957,501 A | 9/1990 | Lahille et al. |
| 4,969,890 A | 11/1990 | Sugita et al. |
| 4,984,581 A | 1/1991 | Stice |
| 4,990,155 A | 2/1991 | Wilkoff |
| 4,994,069 A | 2/1991 | Ritchart et al. |
| 4,994,071 A | 2/1991 | MacGregor |
| 5,002,556 A | 3/1991 | Ishida et al. |
| 5,015,253 A | 5/1991 | MacGregor |
| 5,019,090 A | 5/1991 | Pinchuk |
| 5,026,377 A | 6/1991 | Burton et al. |
| 5,035,706 A | 7/1991 | Giantureo et al. |
| 5,037,377 A | 8/1991 | Alonso |
| 5,041,084 A | 8/1991 | DeVries et al. |
| 5,041,126 A | 8/1991 | Gianturco |
| 5,061,275 A | 10/1991 | Wallstén et al. |
| 5,064,435 A | 11/1991 | Porter |
| 5,071,407 A | 12/1991 | Termin et al. |
| 5,100,429 A | 3/1992 | Sinofsky et al. |
| 5,104,404 A | 4/1992 | Wolff |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,364 A | 7/1992 | Palermo et al. |
| 5,133,731 A | 7/1992 | Butler et al. |
| 5,133,732 A | 7/1992 | Wiktor |
| 5,141,502 A | 8/1992 | Macaluso, Jr. |
| 5,143,085 A | 9/1992 | Wilson |
| 5,147,370 A | 9/1992 | McNamara et al. |
| 5,151,105 A | 9/1992 | Kwan-Gett |
| 5,151,152 A | 9/1992 | Kaeufe et al. |
| 5,152,784 A | 10/1992 | Tsilibary |
| 5,160,341 A | 11/1992 | Brenneman et al. |
| 5,170,801 A | 12/1992 | Casper et al. |
| 5,171,273 A | 12/1992 | Silver et al. |
| 5,176,625 A | 1/1993 | Brisson |
| 5,176,661 A | 1/1993 | Evard et al. |
| 5,181,921 A | 1/1993 | Makita et al. |
| 5,183,085 A | 2/1993 | Timmermans |
| 5,186,992 A | 2/1993 | Kite, III |
| 5,188,621 A | 2/1993 | Samson |
| 5,192,290 A | 3/1993 | Hilal |
| 5,197,977 A | 3/1993 | Hoffman, Jr. et al. |
| 5,197,978 A | 3/1993 | Hess |
| 5,203,772 A | 4/1993 | Hammerslag et al. |
| 5,211,658 A | 5/1993 | Clouse |
| 5,217,484 A | 6/1993 | Marks |
| 5,222,969 A | 6/1993 | Gillis |
| 5,222,970 A | 6/1993 | Reeves |
| 5,224,953 A | 7/1993 | Morgentaler |
| 5,226,911 A | 7/1993 | Chee et al. |
| 5,226,913 A | 7/1993 | Pinchuk |
| 5,228,453 A | 7/1993 | Sepetka |
| 5,234,456 A | 8/1993 | Silvestrini |
| 5,238,004 A | 8/1993 | Sahatjian et al. |
| 5,250,071 A | 10/1993 | Palermo |
| 5,256,146 A | 10/1993 | Ensminger et al. |
| 5,258,042 A | 11/1993 | Mehta |
| 5,261,916 A | 11/1993 | Engelson |
| 5,275,173 A | 1/1994 | Samson et al. |
| 5,304,194 A | 4/1994 | Chee et al. |
| 5,312,152 A | 5/1994 | Woebkenberg, Jr. et al. |
| 5,312,415 A | 5/1994 | Palermo |
| 5,314,472 A | 5/1994 | Fontaine |
| 5,322,501 A | 6/1994 | Mahmud-Durrani |
| 5,336,205 A | 8/1994 | Zenzen et al. |
| 5,341,818 A | 8/1994 | Abrams et al. |
| 5,342,387 A | 8/1994 | Summers |
| 5,350,397 A | 9/1994 | Palermo et al. |
| 5,354,295 A | 10/1994 | Guglielmi et al. |
| 5,354,309 A | 10/1994 | Schnepp-Pesch et al. |
| 5,368,049 A | 11/1994 | Raman et al. |
| 5,373,856 A | 12/1994 | Grenouillet |
| 5,382,259 A | 1/1995 | Phelps et al. |
| 5,383,887 A | 1/1995 | Nadal |
| 5,395,390 A | 3/1995 | Simon et al. |
| 5,405,377 A | 4/1995 | Cragg |
| 5,409,015 A | 4/1995 | Palermo |
| 5,411,475 A | 5/1995 | Atala et al. |
| 5,413,597 A | 5/1995 | Krajicek |
| 5,415,664 A | 5/1995 | Pinchuk |
| 5,417,708 A | 5/1995 | Hall et al. |
| 5,423,829 A | 6/1995 | Pham et al. |
| 5,433,723 A | 7/1995 | Lindenberg et al. |
| 5,441,516 A | 8/1995 | Wang et al. |
| 5,443,478 A | 8/1995 | Purdy |
| 5,443,498 A | 8/1995 | Fontaine |
| 5,484,449 A | 1/1996 | Amundson et al. |
| 5,500,013 A | 3/1996 | Buscemi et al. |
| 5,514,115 A | 5/1996 | Frantzen et al. |
| 5,514,176 A | 5/1996 | Bosley, Jr. |
| 5,520,194 A | 5/1996 | Miyata et al. |
| 5,522,822 A | 6/1996 | Phelps et al. |
| 5,522,836 A | 6/1996 | Palermo |
| 5,523,092 A | 6/1996 | Hanson et al. |
| 5,527,336 A | 6/1996 | Rosenbluth et al. |
| 5,540,701 A | 7/1996 | Sharkey et al. |
| 5,540,713 A | 7/1996 | Schnepp-Pesch et al. |
| 5,545,210 A | 8/1996 | Hess et al. |
| 5,549,624 A | 8/1996 | Mirigian e al. |
| 5,562,641 A | 10/1996 | Flomenblit et al. |
| 5,562,698 A | 10/1996 | Parker |
| 5,569,245 A | 10/1996 | Guglielmi et al. |
| 5,578,074 A | 11/1996 | Mirigian |
| 5,582,619 A | 12/1996 | Ken |
| 5,601,593 A | 2/1997 | Freitag |

| | | |
|---|---|---|
| 5,603,694 A | 2/1997 | Brown et al. |
| 5,607,445 A | 3/1997 | Summers |
| 5,609,627 A | 3/1997 | Goicoechea et al. |
| 5,613,981 A | 3/1997 | Boyle et al. |
| 5,624,461 A | 4/1997 | Mariant |
| 5,637,113 A | 6/1997 | Tartaglia et al. |
| 5,638,827 A | 6/1997 | Palmer et al. |
| 5,639,277 A | 6/1997 | Mariant et al. |
| 5,643,254 A | 7/1997 | Scheldrup et al. |
| 5,643,339 A | 7/1997 | Kavteldaze et al. |
| 5,645,564 A | 7/1997 | Northrup et al. |
| 5,649,949 A | 7/1997 | Wallace et al. |
| 5,653,726 A | 8/1997 | Kieturakis |
| 5,653,727 A | 8/1997 | Wiktor |
| 5,662,621 A | 9/1997 | Lafontaine |
| 5,666,968 A | 9/1997 | Imran et al. |
| 5,667,522 A | 9/1997 | Flomenblit et al. |
| 5,676,697 A | 10/1997 | McDonald |
| 5,690,643 A | 11/1997 | Wijay |
| 5,690,666 A | 11/1997 | Berenstein et al. |
| 5,690,671 A | 11/1997 | McGurk et al. |
| 5,693,085 A | 12/1997 | Buirge et al. |
| 5,702,373 A | 12/1997 | Samson |
| 5,702,414 A | 12/1997 | Richter et al. |
| 5,713,907 A | 2/1998 | Hogendijk et al. |
| 5,716,410 A | 2/1998 | Wang et al. |
| 5,722,989 A | 3/1998 | Fitch et al. |
| 5,725,546 A | 3/1998 | Samson |
| 5,733,329 A | 3/1998 | Wallace et al. |
| 5,743,905 A | 4/1998 | Eder et al. |
| 5,746,765 A | 5/1998 | Kleshinski et al. |
| 5,746,769 A | 5/1998 | Ton et al. |
| 5,749,883 A | 5/1998 | Halpern |
| 5,749,891 A | 5/1998 | Ken et al. |
| 5,749,894 A | 5/1998 | Engelson |
| 5,749,918 A | 5/1998 | Hogendijk et al. |
| 5,749,921 A | 5/1998 | Lenker et al. |
| 5,776,161 A | 7/1998 | Globerman |
| 5,788,653 A | 8/1998 | Lorenzo |
| 5,797,957 A | 8/1998 | Palmer et al. |
| 5,800,455 A | 9/1998 | Palermo et al. |
| 5,800,526 A | 9/1998 | Anderson et al. |
| 5,814,062 A | 9/1998 | Sepetka et al. |
| 5,824,059 A | 10/1998 | Wijay |
| 5,944,733 A | 8/1999 | Engelson |
| 5,947,963 A | 9/1999 | Guglielmi |
| 5,976,131 A | 11/1999 | Guglielmi et al. |
| 5,984,929 A | 11/1999 | Bashiri et al. |
| 5,989,242 A | 11/1999 | Saadat et al. |
| 6,059,815 A | 5/2000 | Lee et al. |
| 6,224,610 B1 * | 5/2001 | Ferrera .................. 606/108 |

OTHER PUBLICATIONS

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978, "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occlusion of Pelvic Bone Tumors"; pp. 322–325 & 661–663.

"Mechanical Devices for Arterial Occlusion" by C. Gianturco, M.D., et al., Jul. 1975, pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'Mini' Gianturco Stainless Steel Coils for Transcatheter Vascular Occlusion" by James H. Anderson, et al., from The Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

"Retrievable Gianturco–Coil Indroducer" by Jeffrey Hawkins, Ronald G. Quisling, MD, J. Parker Mickle, MD, Irvin F. Hawkins, MD, from the Department of Radiology at the University of Florida Medical Center and Hawk Prototype Equipment 1986.

* cited by examiner

APPARATUS FOR DEPLOYMENT OF MICRO-COIL USING A CATHETER

RELATED APPLICATIONS

This is a continuation in part of Ser. No. 09/143,904 filed Aug. 31, 1998, U.S. Pat. No. 6,224,610 and Ser. No. 09/501,466 filed Feb. 9, 2000, which is a continuation in part of Ser. No. 09/218,117 filed Dec. 21, 1998, U.S. Pat. No. 6,296,622.

BACKGROUND OF THE INVENTION

1. Field of the Invention

This invention relates generally to devices for interventional therapeutic treatment or vascular surgery for treatment of defects in the vasculature, and more particularly concerns a system and method for delivering intravascular interventional devices, such as for treatment of aneurysms.

2. Description of Related Art

Vascular interventional devices such as vasoocclusive devices are typically placed within the vasculature of the human body by use of a catheter. Vascular interventional devices such as stents can be placed within an occluded vessel to facilitate blood flow through the vessel, and vasoocclusive devices are typically either placed within a blood vessel to block the flow of blood through a vessel making up that portion of the vasculature through the formation of an embolus, or are placed within an aneurysm stemming from the vessel to form such an embolus within the aneurysm. Stents can have a wide variety of configurations, but generally need to be placed and then released at a desired location within a blood vessel. Vasoocclusive devices used for these procedures can also have a wide variety of configurations, and aneurysms have been treated with external surgically placed clips, detachable vasoocclusive balloons and embolus generating vasoocclusive devices such as one or more vasoocclusive coils.

The delivery of such vasoocclusive devices have typically been accomplished by a variety of means, including via a catheter in which the device is pushed through an opening at the distal end of the catheter by a pusher to deploy the device. The vasoocclusive devices can be produced in such a way that they will pass through the lumen of a catheter in a linear shape and take on a complex shape as originally formed after being deployed into the area of interest, such as an aneurysm.

Some conventional vasoocclusive devices are operated by pulling or jerking the catheter tip from the balloon, thus potentially compromising the position of the implant. One such device provides for an endovascular wire and tip that can be separated from the holding wire mechanically or electrolytically for the formation of thrombus in blood vessels. However, such devices that release the interventional device by mechanically breaking an intermediate section between the catheter tip and balloon can potentially leave broken or jagged ends that can potentially injure the vasculature.

One conventional releasable balloon catheter used to embolize vascular lesions has a tube portion made of a material such as a hydrophilic polymer, located between the catheter and the balloon, that can be broken by torsion of the tube. The tube can be melted by heating the tube, or can be dissolved in the blood when heated, and electrodes are provided for heating the tube. Another conventional technique for separating a balloon from a balloon catheter involves the melting and breaking of a connecting member made from polyvinyl alcohol or trans-polyisoprene between the balloon and the catheter body, when power is supplied to electrodes provided for heating the connecting member. When the connecting member is heated to temperatures of about 70° C. and slight tension is applied, the balloon can be separated from the main catheter body. However, such devices that release the interventional device by melting or dissolving the intermediate section between the catheter tip and balloon can also potentially release undesirable particles of materials into the bloodstream.

There is therefore a need for a precise method of deploying therapeutic interventional devices without compromising the position of the implant, without presenting broken or jagged ends that can potentially injure the vasculature, and without releasing undesirable particles of materials into the bloodstream.

The transmittal of energy of various types through a catheter to a remote location in the body has been used in the past, both for therapeutic purposes and to perform actuation or chemical reactions for delivery systems. In one such system, a temporary stent formed from a coil of tubular thermoplastic material is delivered activated for use by a heating element. The thermoplastic stent body is introduced into the vessel to be supported and is then heated by the heating element above its softening temperature and expanded to a second dimension in order to support the vessel. Cooling of the stent body allows the stent to temporarily support the vessel, and the stent body can be heated at a later time to soften and remove the stent from the vessel. However, the thermoplastic stent body contains an electrical resistance heating element, and heat is generated in the stent by a current is passed through electrically conductive wires.

An endovascular stent and delivery system is also known in which a partially cured material is delivered to a selected site in a blood vessel and is then crosslinked in the blood vessel by laser light energy delivered to the partially cured material. The delivery system can also use thermal energy as from a resistive heating element, radio frequency energy, or beta rays in order to cause the crosslinking.

A flexible guide is also known that is formed from a two-way shape memory alloy for use in non-invasive procedures. The device comprises an elongated, flexible guide having a core of a shape memory alloy which allows for tip-deflection and rotational movement to the guide wire in response to heating provided by transmission of an electrical current through the shape memory alloy.

Another catheter is known that is composed of a main body fitted with a shape memory alloy, with a liquid injector for supplying a warming liquid such as a physiological saline or transfusion solution when the shape memory alloy is to recover an original shape.

In another delivery system for an occlusive device, energy is transmitted through a catheter to a coil and a polymeric material to occlude an aneurysm. The polymeric material is solidified by light, heat or RF energy emitted from the end of a light or energy emitting device placed outside the distal end of the guiding catheter.

A common problem with such known delivery and activation systems, conveying heat by such methods as warm liquids, light, electrical energy, radio frequency energy or beta rays, is that they are typically highly inefficient or not particularly powerful, so that once a device to be delivered is placed in the desired location, there can be a delay while sufficient thermal energy is conducted to the activation site, or in the process heat energy can be radiated or otherwise lost during transmission. It would therefore be desirable to provide a thermal energy activated delivery system for vascular interventional devices that is highly efficient and immediate, and can allow the delivery of a necessary amount of thermal energy to a specific location for deployment of an interventional device.

Heat pipes are known as extremely efficient heat transfer devices, and are much more efficient than solid metal heat sinks, for example. Such heat pipes typically have a hollow interior chamber that has been evacuated, then filled with a small amount of working fluid, and sealed. When heat is applied to one end, serving as an evaporator end, the fluid vaporizes, and carries the heat in the vaporized working fluid extremely rapidly to the other end, serving as a condenser end, where the latent beat of vaporization is released as the vapor condenses back into liquid form. The working fluid is then carried back in liquid form to the evaporator end by capillary action. There is thus a need for application of a flexible heat pipe for conducting heat to a specific desired site for the purpose of deploying interventional devices such as stents and occlusive devices. The present invention meets these and other needs.

SUMMARY OF THE INVENTION

Briefly, and in general terms, the present invention provides a precise system and method for efficiently and cleanly releasing a therapeutic device such as a vasoocclusive coil, a stent, or other therapeutic device for use in interventional therapy and vascular surgery, and which is particularly adapted to be inserted into a portion of a vasculature for treatment of a body vessel such as an aneurysm without compromising the position of the implant.

In a presently preferred aspect of the invention, the intravascular delivery system for release and deployment of a therapeutic device within the vasculature of a patient comprises an elongated, flexible heatpipe pusher member; a therapeutic device to be placed within the vasculature of a patient; and a shape memory device detachably mounting the therapeutic device for placement of the therapeutic device within the vasculature, the shape memory device having a closed configuration connecting the therapeutic device to the flexible heat pipe pusher member, and an open configuration for detaching and deploying the therapeutic device from the flexible heat pipe pusher member when a desired placement of the therapeutic device within the vasculature is achieved. The shape memory device is typically a shape memory collar disposed on one of the therapeutic device and the flexible heat pipe pusher member and connects the therapeutic device and the heat pipe pusher member, and in a presently preferred embodiment, the shape memory device is a shape memory collar disposed on the distal tip of the flexible heat pipe pusher member and connecting the therapeutic device to the flexible heat pipe pusher member. In a presently preferred embodiment, the shape memory collar is made of nickel titanium alloy.

In a presently preferred aspect of the invention, the elongated, flexible heat pipe pusher member comprises a flexible heat pipe having a hollow interior chamber containing a working fluid, the flexible heat pipe having a metal evaporator end portion for conducting heat to the working fluid in the interior chamber of the heat pipe, a flexible insulated mid-portion, and a metal condenser end portion for conducting heat from the working fluid to the shape memory device. In another presently preferred aspect, the insulated mid-portion comprises an outer covering of resinous material so that the mid-portion does not radiate heat. The flexible heat pipe typically comprises a metal hollow tube, and in a presently preferred embodiment, the metal hollow tube is formed from a beryllium copper alloy. In another presently preferred aspect, the evaporator end portion comprises a stainless steel portion for conducting heat to the metal hollow tube and the working fluid in the interior chamber of the heat pipe, and the condenser end portion is partially covered with polytetrafluoroethylene, leaving a distal end portion of the condenser end portion exposed to transfer heat to the shape memory collar.

The shape memory collar can be heated to thereby assume a configuration disconnecting the therapeutic device and the flexible heat pipe pusher member, and the heat pipe pusher member advantageously can be connected to a heat source for transferring heat to the collar to induce the collar to detach the therapeutic device from the flexible heat pipe pusher member. In one presently preferred embodiment, the therapeutic device comprises a stem, and the collar clamps onto the stem. The therapeutic device can comprise a vasoocclusive coil, a stent, or another similar therapeutic device adapted to be placed in the vasculature.

The invention thus also provides for a method for release and deployment of a therapeutic device within the vasculature of a patient. In a presently preferred embodiment, the steps of the method comprise providing a therapeutic device to be placed within the vasculature of a patient; providing an elongated, flexible heat pipe pusher member; providing a shape memory device; detachably mounting the shape memory device to one of the therapeutic device and the elongated, flexible heat pipe pusher member, the shape memory device having a closed configuration connecting the therapeutic device to the flexible heat pipe pusher member, and an open configuration for detaching and deploying the therapeutic device from the flexible heat pipe pusher member when a desired placement of the therapeutic device within a patient's vasculature is achieved; positioning the therapeutic device at a desired placement within a patient's vasculature; and disconnecting the therapeutic device from the elongated, flexible heat pipe pusher member, thereby deploying the therapeutic device. In a presently preferred aspect of the method of the invention, the step of disconnecting the therapeutic device from the elongated, flexible heat pipe pusher member comprises causing heat to be transmitted through the flexible heat pipe member to the shape memory collar to heat the shape memory collar to cause the shape memory collar to expand to release the therapeutic device.

The present invention also provides for an apparatus for release and deployment of a therapeutic device within the vasculature of a patient, comprising an elongated, flexible pusher member having an interior lumen and a distal portion, and a connector fiber detachably mounting the therapeutic device to the pusher member for placement of the therapeutic device within the vasculature, the connector fiber being capable of being broken by heat. An elongated, flexible heat pipe member is disposed within the interior lumen of the elongated, flexible pusher member, and has a distal heating end disposed adjacent to the connector fiber for heating the connector fiber to cause the connector fiber to break and release the therapeutic device for detaching and deploying the therapeutic device from the flexible pusher member when a desired placement of the therapeutic device within the vasculature is achieved. In a presently preferred aspect, the connector fiber is formed from a thermoplastic material, such as polyethylene. In another presently preferred aspect, the pusher member includes at least one entry port communicating with the interior lumen of the pusher member, and the distal heating end of the heat pipe member is disposed in the interior lumen of the pusher member adjacent to the at least one entry port. In a preferred embodiment, the connector fiber extends from a proximal portion of the pusher member to form a loop through the connector ring, and back through the at least one port through the pusher member to the proximal portion of the pusher member. In another preferred aspect, the therapeutic device to be placed within the vasculature of a patient is connected to an annular connector ring, and the connector fiber mounting the therapeutic device to the pusher member passes through the connector ring to secure the therapeutic device to the pusher member.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
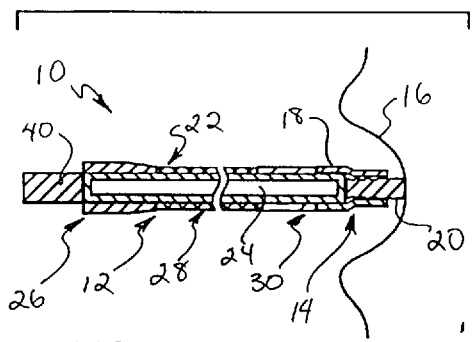
FIG. 1 is an exploded side sectional view of a first preferred embodiment of the heat pipe activated interventional device delivery system of the present invention in which a portion of a therapeutic device is detachably gripped by a shape memory collar mounted to the heat transfer member of the delivery system, showing the shape memory collar in a closed configuration gripping the therapeutic device.

Vasoocclusive devices that are operated by pulling or jerking the catheter tip from the balloon can compromise the position of the implant, while other devices that release such devices by breaking an intermediate section between the catheter tip and balloon can potentially injure the vasculature, and those that melt or dissolve an intermediate section can release undesirable particles of materials into the bloodstream. While the transmittal of energy of various types through a catheter to a remote location in the body has been used in the past, both for therapeutic purposes and to perform actuation or chemical reactions for delivery systems, a common problem with such known delivery and activation systems is that they are typically particularly inefficient.

As is illustrated in the drawings, which are provided for the purposes of illustration and not by way of limitation, the invention is accordingly embodied in an intravascular delivery system for release and deployment of a therapeutic device within the vasculature of a patient. According to the invention, a shape memory collar may be disposed on either the therapeutic device or a flexible heat pipe pusher member, and releasably connects the therapeutic device and the heat pipe pusher member together.

Figure 2:
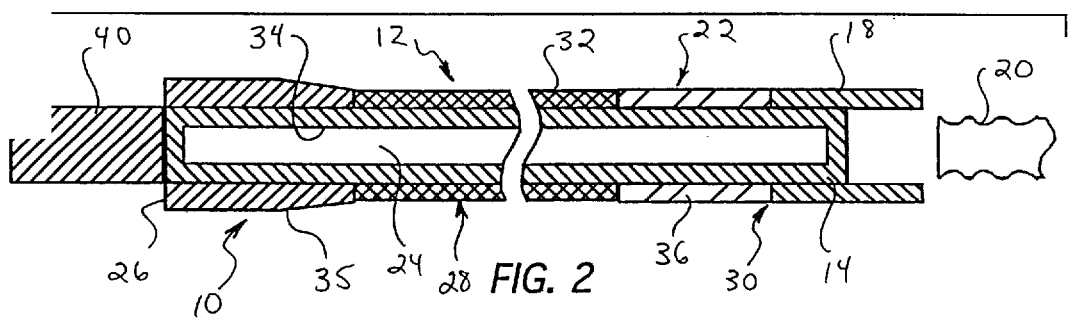
FIG. 2 is an enlarged side sectional view of the heat pipe activated interventional device delivery system of FIG. 1, showing the shape memory collar in an open configuration.

Referring to FIGS. 1 and 2, in a first preferred embodiment, the intravascular delivery system 10 comprises an elongated, flexible heat pipe pusher member 12, having a distal tip 14, and a therapeutic device, such as a coil 16, having at least one configuration which may serve as a vasoocclusive coil or a stent, for example, to be placed within the vasculature of a patient. The therapeutic device is detachably mounted to the distal tip of the pusher member by a shape memory collar 18, for placement of the therapeutic device within the vasculature. The shape memory collar is preferably tubular, having a closed configuration or narrowed configuration with a relatively smaller inner diameter as shown in FIG. 1, connecting the therapeutic device to the flexible heat pipe pusher member, and an open configuration, with a relatively larger inner diameter as shown in FIG. 2, for detaching and deploying the therapeutic device from the flexible heat pipe pusher member when a desired placement of the therapeutic device within the vasculature is achieved. The shape memory collar can, for example, be made of nickel titanium alloy, and the therapeutic device can, for example, be a stent, vasoocclusive coil or wire, having a stem 20 to which a wire coil is mechanically attached, although the wire coil could also be suitably soldered or welded to the stem. The shape memory collar is preferably heat treated in an unextended position, and can be heated to a temperature that allows it to be worked and crimped into an extended position gripping over the end of the stem of the wire coil to connect the therapeutic device to a flexible heat pipe pusher member of the placement catheter shaft.

The elongated, flexible heat pipe pusher member preferably comprises a flexible heat pipe 22 or rod, having a hollow interior chamber 24 that has been evacuated, filled with a small amount of a working fluid, and then sealed. The flexible heat pipe has a metal evaporator end portion 26 for conducting heat to the working fluid in the interior chamber of the heat pipe, a flexible insulated mid-portion 28, and a metal condenser end portion 30 for conducting heat from the working fluid to the shape memory device. The insulated mid-portion preferably has an outer covering 32 of flexible, resinous material so that the mid-portion does not radiate heat. The flexible heat pipe typically is formed from a hollow metal tube 34, and in a presently preferred embodiment, the hollow metal tube is made of an alloy of beryllium and copper. The evaporator end portion preferably comprises a stainless steel portion 35 for conducting heat to the metal hollow tube and the working fluid in the interior chamber of the heat pipe, and the stainless steel evaporator end portion can be formed from a ground stainless steel hypo tube. The condenser end portion is preferably partially covered with polytetrafluoroethylene (PTFE) 36, leaving a distal end portion 38 of the condenser end portion exposed to transfer heat to the shape memory collar.

When the therapeutic device is delivered to an appropriate location in the vasculature, and an operator is satisfied that the device is properly placed, the shape memory collar can be heated, and thereby induced to shrink and pull back to assume a configuration disconnecting the therapeutic device from the placement catheter shaft. The proximal evaporator end of the flexible heat pipe pusher member can thus be connected to a heat source 40, such as an RF heat source or ultrasound heat source, for example, for conducting heat from the proximal evaporator end to the distal condenser end of the flexible heat pipe pusher member and to the shape memory collar at the distal end of the pusher member, to thus heat the collar to return to its previous shape and induce the collar to detach the therapeutic device from the shape memory collar. Heating of the collar can at the same time heat the therapeutic device to cause the therapeutic device to change to a desired configuration.

Figure 3:
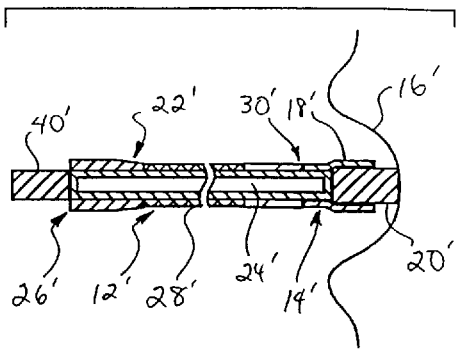
FIG. 3 is an exploded side sectional view of a second preferred embodiment of the heat pipe activated interventional device delivery system of the present invention in which a shape memory collar is mounted to a therapeutic device detachably mounted to the heat transfer member of the delivery system, showing the shape memory collar in a closed configuration gripping the heat transfer member.
Figure 4:
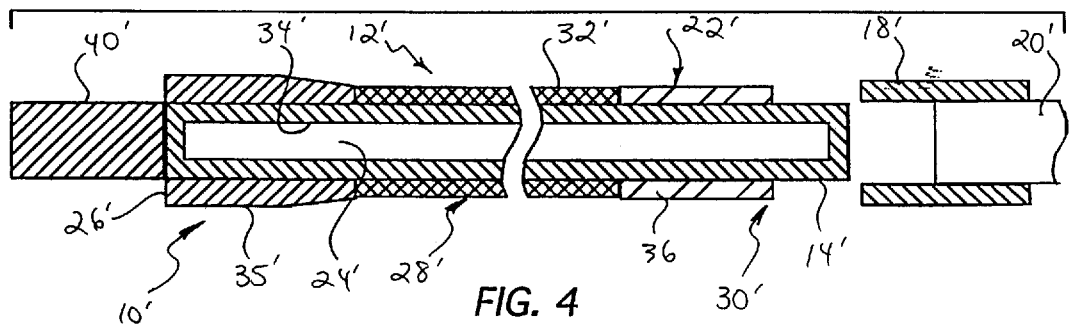
FIG. 4 is an enlarged side sectional view of the heat pipe activated interventional device delivery system of FIG. 3, showing the shape memory collar in an open configuration.
Figure 5:
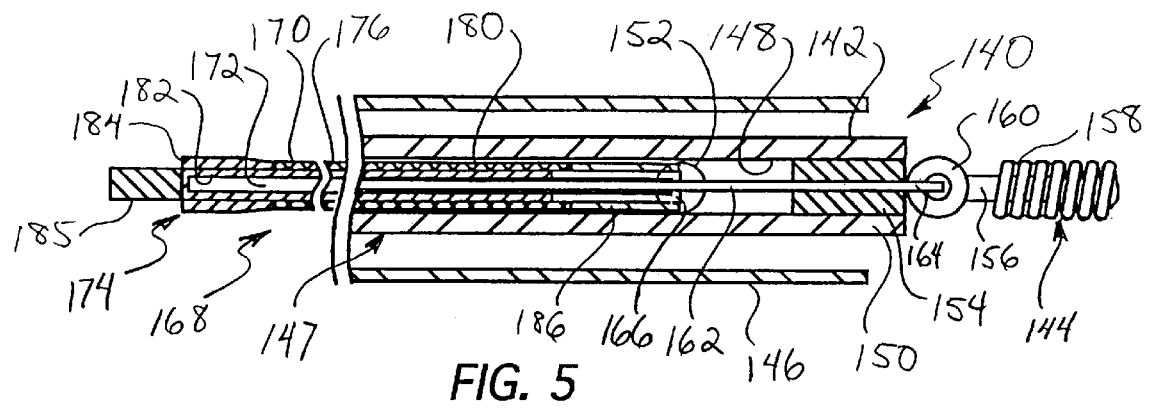
FIG. 5 is a top sectional view of a second embodiment of the apparatus for release and deployment of a therapeutic device.
Figure 6:
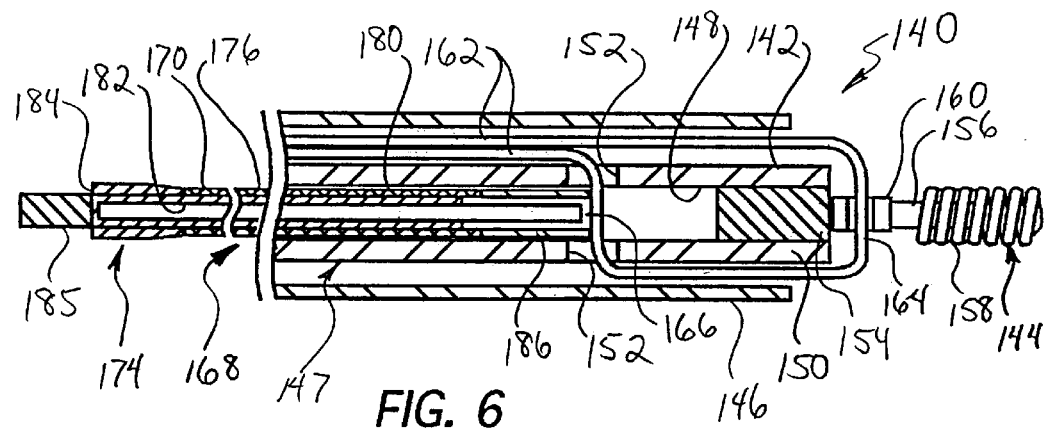
FIG. 6 is a side sectional view of the apparatus of FIG. 5.
Figure 7:
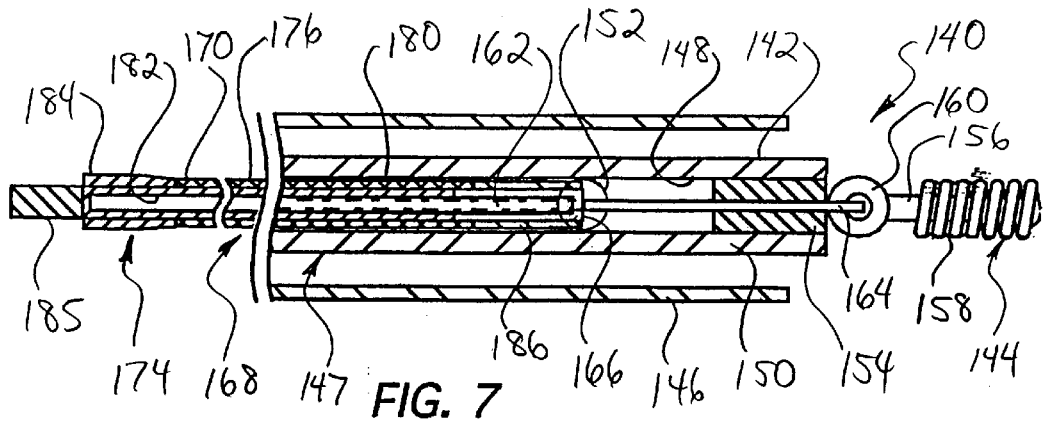
FIG. 7 is a bottom sectional view of the apparatus of FIG. 5.
Figure 8:
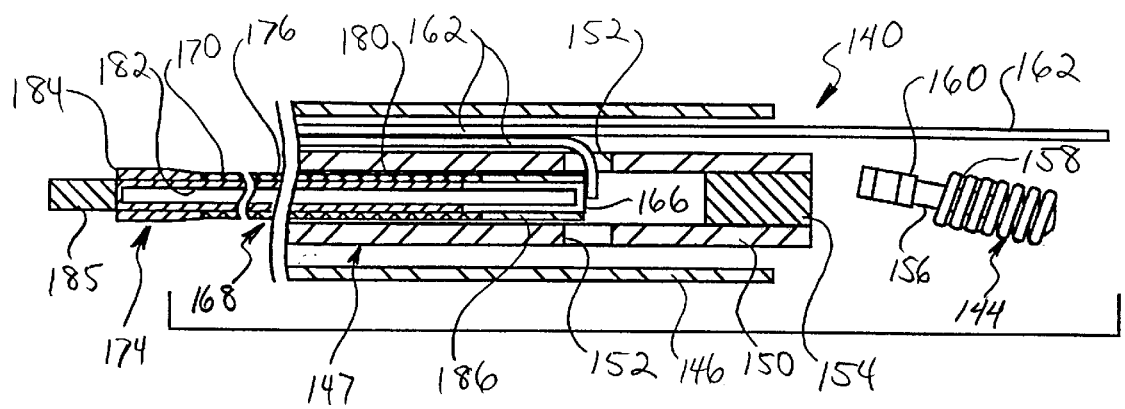
FIG. 8 is a side sectional view of the apparatus of FIG. 5, illustrating release of the therapeutic device upon heating of the elongated connector fiber.

Referring to FIGS. 3 and 4, in a second preferred embodiment, the intravascular delivery system 10' comprises an elongated, flexible heat pipe pusher member 12', having a distal tip 14', and a therapeutic device, such as a coil 16', having at least one configuration which may serve as a vasooclusive coil or a stent, for example, to be placed within the vasculature of a patient.

In the second preferred embodiment, the shape memory collar 18' can be disposed on the stem 20' of the therapeutic device, and is adapted to be crimped and thus detachably mounted to the distal end 14' of the flexible heat pipe pusher member, for placement of the therapeutic device within the vasculature. The shape memory collar is preferably tubular, having a closed configuration or narrowed configuration with a relatively smaller inner diameter as shown in FIG. 3, connecting the therapeutic device to the flexible heat pipe pusher member, and an open configuration, with a relatively larger inner diameter as shown in FIG. 4, for detaching and deploying the therapeutic device from the flexible heat pipe pusher member when a desired placement of the therapeutic device within the vasculature is achieved. The shape memory collar is preferably heat treated in an unextended position, and can be heated to a temperature that allows it to be worked and crimped into an extended position gripping over the end of the stem of the wire coil to connect the therapeutic device to a flexible heat pipe pusher member of the placement catheter shaft.

The elongated, flexible heat pipe pusher member preferably comprises a flexible heat pipe 22' or rod, having a hollow interior chamber 24' that has been evacuated, filled with a small amount of a working fluid, and then sealed. The flexible heat pipe has a metal evaporator end portion 26' for conducting heat to the working fluid in the interior chamber of the heat pipe, a flexible insulated mid-portion 28', and a metal condenser end portion 30' for conducting heat from the working fluid to the shape memory device. The insulated mid-portion preferably has an outer covering 32' of flexible, resinous material so that the mid-portion does not radiate heat. The flexible heat pipe typically is formed from a hollow metal tube 34', and in a presently preferred embodiment, the hollow metal tube is made of an alloy of beryllium and copper. The evaporator end portion preferably comprises a stainless steel portion 35' for conducting heat to the metal hollow tube and the working fluid in the interior chamber of the heat pipe, and the stainless steel evaporator end portion can be formed from a ground stainless steel hypo tube. The condenser end portion is preferably partially covered with a coating 36' of PTFE, leaving a distal end portion 38' of the condenser end portion exposed to transfer heat to the shape memory collar.

The proximal evaporator end of the flexible heat pipe pusher member can be connected to a heat source 40', such as an RF heat source or ultrasound heat source, for example, for conducting heat from the proximal evaporator end to the distal condenser end of the flexible heat pipe pusher member and to the shape memory collar at the distal end of the pusher member, to thus heat the collar to return to its previous shape and induce the collar to detach the therapeutic device from the shape memory collar.

In a presently preferred embodiment, the shape memory collar is formed from a shape memory material such as nickel titanium alloy, that can be heat treated to have shape memory behavior, such that the alloy has a desired closed configuration at a temperature appropriate for introduction into the body, and after placement, the collar will take on a more open shape for detaching the therapeutic device from the flexible, heat pipe pusher member. Those skilled in the art will recognize that the invention can also be used with a variety of other placement catheter systems, and it is not intended that the invention be limited to the placement concepts illustrated by way of example.

In another presently preferred embodiment, the invention is embodied in an apparatus for deployment of a therapeutic device such as a micro-coil using a catheter by connecting the therapeutic device to a distal portion of a pusher member by a connector fiber that can be broken by heating a portion of the connector fiber to break the connector fiber and thereby release the therapeutic device for placement in the vasculature.

With reference to FIGS. 5–8, the invention accordingly provides for an apparatus 140 including an elongated, flexible pusher member 142 for release and deployment of a therapeutic device 144 such as a vasoocclusive device, which may for example be a microcoil, only a portion of which is shown, within the vasculature of a patient, through a delivery catheter 146. The pusher member has a shaft 147 that provides a measure of thermal insulation to an interior lumen 148, as will be further explained below. The shaft of the pusher member typically has an outer diameter of approximately 0.015", and an inside diameter of approximately 0.007, and can be formed from polyethylene terephthalate (PET) tubing. The pusher member has a distal portion 150 with entry ports 152 in communication with the interior lumen, and a plug 154 at the distal end of the pusher member, typically secured within the distal end of the pusher member by adhesive, such as a cyanoacrylate adhesive, for example.

The therapeutic device is typically connected to a stem 156 such as by solder 158, and the stem is in turn connected to an annular connector ring 160, typically by an adhesive such as a cyanoacrylate adhesive, for example. The therapeutic device is mounted and secured to the distal portion of the pusher member by an elongated connector thread or fiber 162 extending from a proximal portion of the pusher member to form a loop 164 through the connector ring, and extending back through the entry ports of the pusher member to the proximal portion of the pusher member. In a presently preferred embodiment, the connector fiber is formed of polyethylene, and is typically about 0.015 to 0.030 inches in diameter, although the connector fiber can be as thin as about 0.0005 inches in diameter, and can be formed from a variety of thermoplastic materials with high tensile strength and suitable melt temperatures. The connector fiber may also optionally be formed of a suitable high tensile strength material, such as a biodegradable material, for example, that would merely degrade or decompose to break upon being heated.

A portion of the connector fiber to be broken to deploy the therapeutic device passes adjacent to the distal heating end 166 of an elongated, flexible heat pipe member 168, such as described above. The elongated, flexible heat pipe member preferably comprises a flexible heat pipe 170 or rod, having a hollow interior chamber 172 that has been evacuated, filled with a small amount of a working fluid, and then sealed. The flexible heat pipe has a metal evaporator end portion 174 for conducting heat to the working fluid in the interior chamber of the heat pipe, a flexible insulated mid-portion 176, and a metal condenser end portion at the distal heating end 166 for conducting heat from the working fluid to the shape memory device. The insulated mid-portion preferably has an outer covering 180 of flexible, resinous material so that the mid-portion does not radiate heat. The flexible heat pipe typically is formed from a hollow metal tube 182, and in a presently preferred embodiment, the hollow metal tube is made of an alloy of beryllium and copper. The evaporator end portion preferably comprises a stainless steel portion 184 for conducting heat to the metal hollow tube and the working fluid in the interior chamber of the heat pipe, and the stainless steel evaporator end portion can be formed from a ground stainless steel hypo tube. The proximal evaporator end of the flexible heat pipe member can be connected to a heat source 185, as noted above. The condenser end portion is preferably partially covered with polytetrafluoroethylene (PTFE) 186, leaving the distal heating end portion of the condenser end portion exposed to transfer heat to cause the connector fiber to break and release the therapeutic device. The lumen of the pusher member advantageously provides an insulative space and wall thickness to contain the heating of the connector fiber to avoid thermal damage to surrounding tissues, and to help contain pieces of the connector fiber that may be formed during heating of the connector fiber to deploy the therapeutic device.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for release and deployment of a therapeutic device within the vasculature of a patient, comprising:

an elongated, flexible pusher member having an interior lumen and a distal portion;

a connector fiber capable of detachably mounting the therapeutic device to the pusher member for placement of the therapeutic device within the vasculature, the connector fiber being capable of being broken by heat;

an elongated, flexible heat pipe member disposed within the interior lumen of the elongated, flexible pusher member, said elongated, flexible heat pipe member having a distal heating end disposed adjacent to the connector fiber for heating the connector fiber to cause the connector fiber to break and release the therapeutic device for detaching and deploying the therapeutic device from the flexible pusher member when a desired placement of the therapeutic device within the vasculature is achieved.

2. The intravascular delivery system of claim 1, wherein said elongated, flexible heat pipe member comprises a flexible heat pipe having a hollow interior chamber containing a working fluid, said flexible heat pipe having a metal evaporator end portion for conducting heat to the working fluid in the interior chamber of the heat pipe, a flexible insulated mid-portion, and a metal condenser end portion for conducting heat from the working fluid to the connector fiber.

3. The intravascular delivery system of claim 2, wherein said insulated mid-portion comprises an outer covering of resinous material so that the mid-portion does not radiate heat.

4. The intravascular delivery system of claim 2, wherein said flexible heat pipe comprises a metal hollow tube.

5. The intravascular delivery system of claim 4, wherein said metal hollow tube is formed from a beryllium copper alloy.

6. The intravascular delivery system of claim 2, wherein said evaporator end portion comprises a stainless steel portion for conducting heat to the working fluid in the interior chamber of the heat pipe.

7. The intravascular delivery system of claim 2, wherein said condenser end portion is partially covered with polytetrafluoroethylene, leaving a distal end portion of the condenser end portion exposed to transfer heat to the connector fiber.

8. The apparatus of claim 1, wherein said connector fiber is formed from a thermoplastic material.

9. The apparatus of claim 1, wherein said connector fiber is formed from polyethylene.

10. The apparatus of claim 1, wherein said pusher member includes at least one entry port communicating with said interior lumen of said pusher member, and said elongated, flexible heat pipe member is disposed in the interior lumen of the pusher member adjacent to said at least one entry port.

11. The apparatus of claim 1, wherein said therapeutic device to be placed within the vasculature of a patient is connected to an annular connector ring, and the connector fiber mounting the therapeutic device to the pusher member passes through the connector ring to secure the therapeutic device to the pusher member.

12. The apparatus of claim 11, wherein said pusher member includes at least one entry port communicating with said interior lumen of said pusher member, and wherein said connector fiber extends from a proximal portion of the pusher member to form a loop through the connector ring, and back through said at least one port through the pusher member to the proximal portion of the pusher member.

13. The apparatus of claim 1, wherein said therapeutic device comprises a vasoocclusive device.

14. The apparatus of claim 1, wherein said therapeutic device comprises a microcoil.

15. A method for release and deployment of a therapeutic device within the vasculature of a patient, the steps of the methods comprising:

providing a therapeutic device to be placed within the vasculature of a patient;

providing an elongated, flexible pusher member having an interior lumen and a distal portion;

providing a connector fiber capable of detachably mounting the therapeutic device to the pusher member for placement of the therapeutic device within the vasculature, the connector fiber being capable of being broken by heating;

providing an elongated, flexible heat pipe member within the interior lumen of the elongated, flexible pusher member, said elongated, flexible heat pipe member having a distal heating end disposed adjacent to the connector fiber for heating the connector fiber;

positioning the therapeutic device at a desired placement within a patient's vasculature; and supplying heat to the elongated, flexible heat pipe member to heat a portion of said connector fiber to cause the connector fiber to break and release the therapeutic device for detaching and deploying the therapeutic device from the flexible pusher member when a desired placement of the therapeutic device within the vasculature is achieved.

16. The method of claim 15, wherein said therapeutic device comprises a vasoocclusive device.

17. The method of claim 15, wherein said therapeutic device comprises a microcoil.

* * * * *